United States Patent [19]

Connery, deceased et al.

[11] 4,195,630
[45] Apr. 1, 1980

[54] MEN'S UNDERGARMENTS

[75] Inventors: Thomas J. Connery, deceased, late of Ft. Lauderdale, Fla.; by Ruth Connery, executrix, 3250 NE. 28th St., Apartment 607, Ft. Lauderdale, Fla. 33308

[73] Assignees: Patricia Connery Koko; Marie H. Koko, both of Oak Park, Ill.; Ruth Connery, Fort Lauderdale, Fla.

[21] Appl. No.: 849,401

[22] Filed: Nov. 7, 1977

Related U.S. Application Data

[63] Continuation-in-part of Ser. No. 751,910, Dec. 17, 1976, abandoned.

[51] Int. Cl.² ................................................ A61F 5/40
[52] U.S. Cl. ........................................ 128/159; 2/403
[58] Field of Search ........................... 2/403, 404, 405; 128/158, 159, 157

[56] References Cited

U.S. PATENT DOCUMENTS

| 850,298 | 4/1907 | De Mars | 128/158 |
| 1,477,187 | 12/1923 | Rayve | 128/159 |
| 2,601,602 | 6/1952 | Firsching | 2/404 X |
| 3,295,520 | 1/1967 | Keller | 2/404 X |
| 3,314,422 | 4/1967 | Phillips | 2/403 |

FOREIGN PATENT DOCUMENTS

| 190014 | 5/1957 | Austria | 2/406 |
| 1014066 | 5/1952 | France | 2/405 |
| 280164 | 4/1952 | Switzerland | 2/405 |
| 459968 | 1/1937 | United Kingdom | 2/405 |

*Primary Examiner*—H. Hampton Hunter
*Attorney, Agent, or Firm*—Shoemaker and Mattare, Ltd.

[57] ABSTRACT

A men's undergarment having a support for supporting the wearer's scrotum/testicles and a protective flap having a penis accommodating pocket thereon. An opening is defined in the scrotum/testicle support through which a penis fits to be encased by the pocket. The flap is anchored at a location above the opening and hangs down freely over that opening.

2 Claims, 3 Drawing Figures

MEN'S UNDERGARMENTS

BACKGROUND OF THE INVENTION

This application is a continuation-in-part of application Ser. No. 751,910, filed Dec. 17, 1976.

The present invention relates in general to garments, and, more particularly, to men's undergarments.

For many years, only minor changes have been made in the design of men's undergarments. Such changes generally take the form of changes in color, shape, location of seams, and the like.

There are only a relatively few undergarment configurations which account for health, comfort and accessibility. Examples of such configurations are undergarments which are intended to provide comfort when the wearer is in a sitting position, flap coverings over penis openings, and those undergarments intended for use by men suffering from various ailments such as kidney, bowel, bladder or prostrate disorders, and the like.

While representing some advance, all of the known prior art undergarments have deficiencies, especially in the area of health protection. All of the known prior art undergarments, even those having flaps, do not provide any means for supporting the genitals while simultaneously protecting the wearer from scalding and infection caused by contact between the wearer's skin and urine.

After urinating, it is not uncommon for several drops of urine to ooze out of the penis. Such urine drops may cause infection if such drops contact either the wearer's legs or his scrotum/testicles.

A further problem not solved by the prior art undergarments is also health-related, and concerns proper air circulation to the genitals of the wearer. All of the known prior art undergarments in some manner inhibit such air circulation, thereby creating problems associated with perspiration, prickly heat, and jock itch. The inventor is not aware of any prior art undergarment which provides the above-discussed support and separation while also providing adequate air circulation. The double fly-front produced in those prior art undergarments having a flap further exacerbates the problems associated with lack of air circulation. skin and urine.

The undergarment embodying the teachings of the present invention comprises a flap attached to a body-encircling element, such as the undergarment body or a waistband, to hang down in front of the wearer's genitals. The flap has the distal end thereof free and the lowermost terminal edge thereof is folded upwardly and attached to the flap body to define a pocket which receives and accommodates the wearer's penis. Scrotum/testicle support is provided by either the undergarment itself, as in the case of briefs, or by a supporter tethered to the undergarment. An opening is defined in either the supporter or the undergarment through which the penis fits to be received and encased by the pocket. The pocket can be positioned so that the penis is supported, or unsupported, as is suitable or comfortable.

The wearer of the undergarment is not only provided support, but is also protected against contact by urine by the pocket, and against prickly heat and the like by the free air circulation provided by the undergarment embodying the teachings of the present invention.

The pocket covers the penis while serving to catch urine and to further separate the penis from the scrotum/testicles. The pocket thus provides, firstly health advantages not heretofore available in prior art undergarments, and secondly comfort advantages which are not available in prior art undergarments. Even those undergarments which include an overhanging flap do not protect against contact with urine. Accordingly, support and health features are provided by the undergarment embodying the teachings of the present invention, which features have not heretofore been obtainable in the prior art undergarments. The flap also provides privacy and easy accessibility as additional features thereof.

OBJECTS OF THE INVENTION

It is therefore a main object of the present invention to provide an undergarment which protects the wearer from contact with urine.

It is another object of the present invention to provide an undergarment which supports a wearer's genitals while allowing air circulation thereto.

It is a further object of the present invention to provide an undergarment which simultaneously provides health protection, support, comfort and privacy.

These together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figure 1:
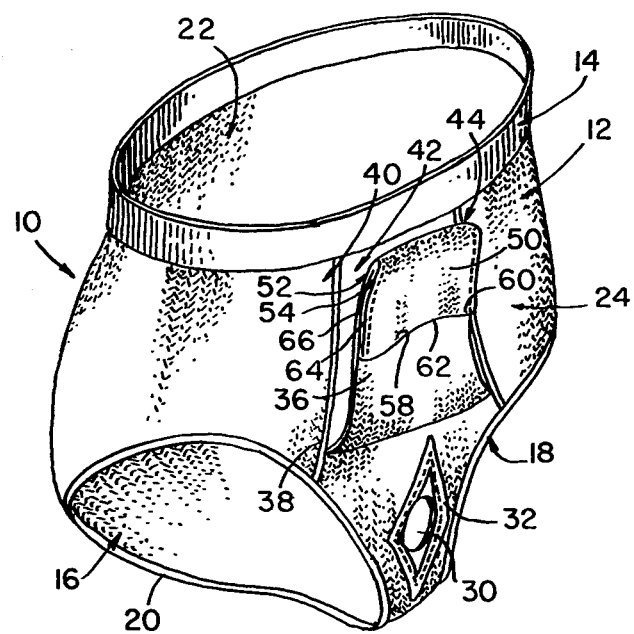
FIG. 1 is a perspective view of a first embodiment of the undergarment embodying the teachings of the present invention.

Shown in FIG. 1 is a men's undergarment 10 which is in the form of briefs, and can be fabricated of knitted material or woven material, or other such material. The undergarment 10 comprises a tubular body portion 12 which encircles a wearer's body, and has a waistband 14 surmounted thereon and a pair of leg openings 16 and 18 defined therein in the usual manner by welts 20, or the like. A seat portion 22 and a frontal portion 24 are also defined on the body portion.

The undergarment 10 has a penis opening 30 defined in the frontal portion and is preferably circular in shape surrounded by a diamond-shaped border defining welt 32 to reinforce that opening.

A single ply front flap 36 is pendantly attached to the frontal portion 24 by stitching strips 38 defined in welts 40 or the like, which extend from adjacent the leg openings to adjacent the waistband, thereby providing the frontal portion with a double ply construction.

As shown in FIG. 1, the front flap 36 has a proximal portion 42 attached to the body frontal section by the stitching and a distal portion 44 pendantly supported to overhang the opening 30. Preferably, the distal portion 44 is approximately equal in length to the proximal portion so that the distal portion extends to a location at or near the lower end of the waistband when folded upwardly as shown in FIG. 1.

By being connected to the body encircling portion of the undergarment for a substantial length of the flap, the flap is not subject to tearing or ripping apart from the undergarment. Such a problem is important after repeated uses or when the undergarment becomes old and has undergone repeated washings, and the like.

The lower free end of the distal portion is underfolded to form a pocket 50 which includes a posterior section 52 and an anterior section 54 formed by the segment of the distal portion located in front of the posterior section. Stitching 56 attaches the lowermost terminal end 58 of the distal portion to the body of the distal portion to form the pocket 50. The terminal end 58 is attached to the distal portion body at the outer edges 60 thereof, with the central segment of the end 58 open to form entrance section 62. Preferably, the edges 64 of the pocket which are coincident with the edges 66 of the distal portion are free and are not stitched thereto, but can be so attached if desired, as shown.

In the preferred embodiment, the entrance section is located to be positioned adjacent opening 30 when the flap 36 overhangs that opening in the operative position.

In use the scrotum/testicles will be supported inside the undergarment, while the penis is located outside the undergarment via the opening 30 and is accommodated and encased in pocket 50. The flap 36 provides privacy. Pocket 50 may be lined with tissue or a liner of plastic, rubber, or the like. Furthermore, the flap 36 may also be attached to the waistband 14. The flap my be attached: (a) to the waistband between the welts 40, then down both welts to a location about one inch from where those welts meet the leg welts 20; or (b) to the frontal section transversely across that section between the welts at a location superjacent the opening 30, then down welts 40 as in (a); or (c) in an inverted "V" from the juncture of the welts 40 and 20 on one leg opening, diagonally upward to a location superjacent welt 32 and opening 30, then diagonally downward to the juncture of the welts 20 and 40 on the other leg opening; or the like.

In a specific embodiment of the undergarment 10, the fabric opening is approximately 1½ inches in diameter, is surrounded by a concave shape welt which has a diagonal length of about 1½ inches at the center thereof and a diagonal length of about 5 inches in the vertical height as measured from the edges adjacent the opening. The unfolded flap extends about 6 inches below the bottom of the opening so that the bottom 3 inches can be folded up and attached by the upper corners thereof to form the pocket 50.

Figure 2:
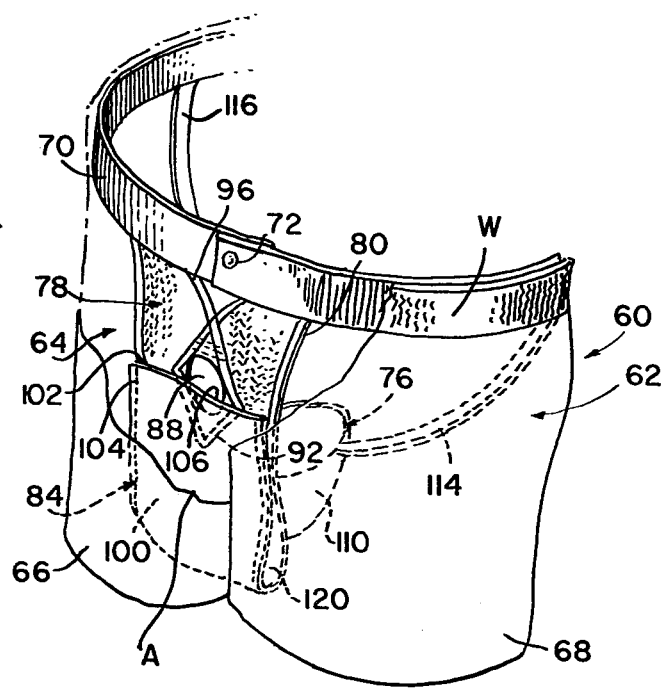
FIG. 2 is a perspective view of another embodiment of the undergarment embodying the teachings of the present invention.

An alternative embodiment of the men's undergarment is shown in FIG. 2 and is indicated by the reference numeral 60. The undergarment 60 includes a body portion 62 comprising a frontal portion 64 and a pair of leg sections 66 and 68 and a waistband W surmounted thereon. The undergarment 60 is in the form of shorts, or the like, and can comprise a fly opening or the like and a waistband fastener for opening that fly opening. A cutline A is defined in FIG. 2 to show that the support is located inside the undergarment 60. The support has a waistband 70 and a waistband fastener 72, both located adjacent garment waistband W. A scrotum/testicle supporter 76 is located inside the undergarment 60 and includes a flap 78 attached to the inside of the frontal portion 64 by stitching and welts 80, or the like. As shown in FIG. 2, the flap extends from subjoining the waistband 70 to near the bottom of the undergarment. The stitching extends for only a portion of the flap so that distal end 84 thereof is freely hanging. An opening 88 is defined in the flap 78 and, like opening 30, is surrounded by a diamond-shaped welt 92. Stitching, such as criss-cross stitching 96, can also be used.

The distal end of the flap 78 is outturned to form a pocket 100 positioned subjacent opening 88 as shown in FIG. 2. As in flap 36, the lowermost terminal end 102 of the flap 78 is attached to the body of the flap at the outer edges 104 of that terminal end to form an entrance section 106 to receive a penis to be accommodated and encased in the pocket 100.

A cup-like supporter 110 is located behind the flap 78 and accommodates the scrotum/testicles in a supporting manner. A pair of support straps 114 and 116 extend between the waistband and the supporter to connect the supporter 110 to the body of the undergarment.

The testicles/scrotum are supported in the supporter 110, and the penis is received in the pocket 100 via opening 88 to be accommodated and encased thereby. The sides 120 of the pocket are shown to be open, but, like the FIG. 1 embodiment, can also be sewn together to form a closed pocket if so desired.

Attachment of the flap 78 to the undergarment 60 can be accomplished in a manner similar to that attachment discussed above in connection with the FIG. 1 embodiment, with dimensions, proportions, and the like being similar thereto. Thus, for example, the pocket 100 can be defined so that terminal end 102 is located immediately adjacent opening 88 to partially cover same if desired.

As in the FIG. 1 embodiment, attachment of the flap to the body encircling portion of the undergarment for a substantial length of the flap protects that flap from tearing or ripping away from the body encircling portion as the undergarment becomes older or after repeated uses of the flap.

Alternatively, the flap 78 can be located on the outside of the undergarment 60 with the supporter 110 located inside the undergarment 60. In such a case, the opening 88 will be defined in the body 62 of the undergarment 60. The terminal end of flap 78 will then be inturned to define the pocket 100 on the posterior section of the flap, as opposed to the outturned section located on the anterior section of the flap shown in FIG. 2.

A further alternative of the FIG. 2 would include just the flap 78 without the supporter 110. The flap would still be located within the undergarment 60 and would only be used to separate the penis from the scrotum/testicles.

Figure 3:
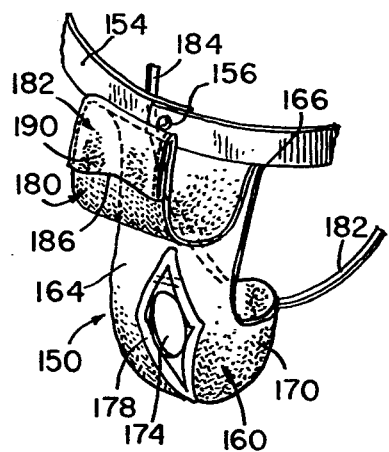
FIG. 3 is a perspective view of still another embodiment of the undergarment embodying the teachings of the present invention.

Another embodiment of the undergarment is shown in FIG. 3 and is generally indicated by the reference numeral 150. The undergarment 150 includes a waistband 154 having a fastener 156 thereon. A scrotum/testicle supporter 160 includes a frontal located body section 164 pendantly supported at top end 166 thereof to the waistband 154 near fastener 156 and having a cup-like supporting section 170 on the other end thereof. An opening 174 is defined in the body section 164 and is bordered by diamond-shaped welt 178 as was aforediscussed. Tether straps 182 and 184 attach the supporter 160 to the waistband, and extend therebetween.

A flap 180 is pendantly attached to the waistband subjacent the fastener 156 to be located in front of the undergarment. The flap has a lower terminal end 182 which is underfolded and is attached to the flap to form a pocket 190. The end 182 is attached to the flap at the outer edges thereof to define an entrance 186 for receiving a penis to be accommodated and encased in the pocket 190.

The scrotum/testicles are supported in the supporter 170 and the penis is received in the pocket 190 via the opening 174 and entrance 186. The undergarment 150 can be worn separately or in combination with other undergarments such as those shown in FIGS. 1 and 2.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

It is claimed:

1. A men's undergarment comprising:
supporting means for supporting a scrotum/testicles, said supporting means including a body encircling portion which is in the form of a brief having an opening defined therein through which a penis is received; an elongate protective flap connected at one end thereof to said supporting means and having another end and sides thereof free and unconnected to said supporting means so that said flap hangs loosely on said supporting means, said flap having an inner surface presented toward said opening, said flap connected end being located above said opening so that said flap hangs downwardly over said opening and completely covers same, said protective flap having said free end folded back over itself to form an extra thickness of material at said free end and fastening means fastening the sides of said extra thickness of material to the sides of said flap with the end of said extra thickness of material being unconnected to said flap to define an open topped pocket on said flap free end, said pocket being formed on said flap inner surface and being free and unconnected to said supporting means, a penis fitting into said pocket via said open top to be accommodated in said pocket so that such testicles/scrotum is supported by said support means and is separated from such penis and such penis is encased in said pocket.

2. The undergarment of claim 1, further including a body encircling portion, said flap connected end being attached to said body encircling portion.

* * * * *